(12) United States Patent
Janssens

(10) Patent No.: US 11,464,600 B2
(45) Date of Patent: Oct. 11, 2022

(54) MECHANICAL INTERFACE DEVICE TO BONE STRUCTURE WITH AN INTEGRATED TARGETING REFERENCE, ALLOWING FOR SURGICAL DEVICE ATTACHMENT

(71) Applicant: Eindhoven Medical Robotics B.V., Eindhoven (NL)

(72) Inventor: Marc Janssens, Eindhoven (NL)

(73) Assignee: Eindhoven Medical Robotics B.V., Eindhoven (NL)

( * ) Notice: Subject to any disclaimer, the term of this patent is extended or adjusted under 35 U.S.C. 154(b) by 49 days.

(21) Appl. No.: 17/253,978

(22) PCT Filed: Jun. 19, 2019

(86) PCT No.: PCT/NL2019/050380
§ 371 (c)(1),
(2) Date: Dec. 18, 2020

(87) PCT Pub. No.: WO2019/245369
PCT Pub. Date: Dec. 26, 2019

(65) Prior Publication Data
US 2021/0361380 A1 Nov. 25, 2021

Related U.S. Application Data

(60) Provisional application No. 62/687,535, filed on Jun. 20, 2018.

(51) Int. Cl.
*A61B 90/00* (2016.01)
*A61B 5/055* (2006.01)

(52) U.S. Cl.
CPC .............. *A61B 90/39* (2016.02); *A61B 5/055* (2013.01); *A61B 2090/3916* (2016.02); *A61B 2090/3933* (2016.02); *A61B 2090/3991* (2016.02)

(58) Field of Classification Search
CPC ......... A61B 90/39; A61B 34/20; A61B 34/30; A61B 34/70; A61B 90/10; A61B 90/50;
(Continued)

(56) References Cited

U.S. PATENT DOCUMENTS 6,546,277 B1 * 4/2003 Franck .................. A61B 90/10
606/130
2005/0215888 A1 9/2005 Grimm et al.
(Continued)

FOREIGN PATENT DOCUMENTS

| DE | 10039737 A1 | 2/2002 | |
|----|-------------|--------|---|
| DE | 10029737 A1 * | 5/2003 | ............. A61B 5/061 |
| WO | 2005046451 A2 | 5/2005 | |

OTHER PUBLICATIONS

International Search Report dated Oct. 4, 2019 for PCT/NL/2019/050380.

(Continued)

*Primary Examiner* — Keith M Raymond
*Assistant Examiner* — Johnathan Maynard
(74) *Attorney, Agent, or Firm* — Suiter Swantz pc llo

(57) ABSTRACT

Device 1 for fixation to the skull 2 of a patient that can serve as a fiducial marker in scan guided surgical operations using a surgical instrument. The device 1 comprises a material translucent for the applied electromagnetic waves of the scan and a fiducial marker and where the device 1 comprises means to fixate the device in a well-defined manner to the surgical instrument.

8 Claims, 5 Drawing Sheets

(58) Field of Classification Search
CPC .......... A61B 2017/0047; A61B 5/4528; A61B 2090/3983; A61B 2034/304; A61B 2090/0811; A61B 17/3423; A61B 5/1127; A61B 2017/2927; A61B 2017/3445; A61B 2090/3933; A61B 2090/3954
See application file for complete search history.

(56) References Cited

U.S. PATENT DOCUMENTS

| | | | |
|---|---|---|---|
| 2011/0098722 A1 | 4/2011 | Ulfarsson et al. | |
| 2013/0096573 A1* | 4/2013 | Kang | A61B 34/30 606/130 |
| 2014/0275964 A1* | 9/2014 | Kim | A61N 5/1007 600/411 |
| 2015/0265366 A1 | 9/2015 | Andrews et al. | |
| 2017/0000497 A1* | 1/2017 | Wolfe | A61B 34/20 |
| 2017/0035525 A1 | 2/2017 | Baumgartner | |
| 2017/0100202 A1 | 4/2017 | Nemanic et al. | |
| 2017/0252114 A1 | 9/2017 | Crawford et al. | |
| 2018/0028266 A1 | 2/2018 | Barnes et al. | |

OTHER PUBLICATIONS

Weber, Stefan et al., "Instrument flight to the inner ear", Sci Robot, Mar. 15, 2017, eaal4916, 28 pages.

* cited by examiner

MECHANICAL INTERFACE DEVICE TO BONE STRUCTURE WITH AN INTEGRATED TARGETING REFERENCE, ALLOWING FOR SURGICAL DEVICE ATTACHMENT

The invention relates to a device for fixation to the skull (bone structure) of a patient that can serve as a fiducial marker in scan guided surgical operations using a surgical instrument (device). The fiducial marker serves as a targeting reference.

Such a device is known from Weber et al., Sci. Robot. 2, eaal4916 (2017) 15 Mar. 2017. The known device consists of four surgical fiducial screws. These screws are used as markers during a Computer Tomography (CT) scan of the skull. The scan is used to guide a surgical instrument, i.e. in this case a drilling robot along a drill trajectory. Once the scan is made the skull of the patient is fixated to an operating table. Then the patient's lateral skull is registered using the bone-anchored fiducial screws to allow for a transfer of the drill trajectory's entry point and a patient optical reference skull attachment point to the situs. The patient optical reference is mounted using a percutaneous 8 mm bone screw. Thus after the scan and the determination of the drilling trajectory many steps are necessary to ensure that the robot drill has the right entry point in the skull and follows the exact drilling trajectory as determined from the scan. These steps take time, complicate the surgical procedure and require the patient to be longer under anaesthetic care.

According to the invention the device comprises a material translucent for the applied electromagnetic waves of the scan and a fiducial marker and where the device comprises means to fixate the device in a well-defined manner to the surgical instrument.

The device comprises a material translucent for the applied electromagnetic waves of the scan. A fiducial marker is added to the device. This can be a traditional fiducial marker like a fiducial screw or a gold seed. In contrast to the traditional use of a fiducial marker this marker does not have to be attached to the skull but can also be attached to the device. The device can be fixed to the surgical instrument in a well-defined manner using for instance screws or clamps. The device can be fixated to the skull by for instance bone screws. The device according to the invention has the advantage that the data acquired with the scan can be directly referenced to the position of the surgical instrument, since the well-defined fixation of the device to the surgical instrument clearly defines the position of the fiducial marker (s), i.e. the position of the skull with respect to the surgical instrument. The device functions as an adapter (mechanical interface) between the skull and the surgical instrument. In the known example according to Weber et al. the scan is obtained with x-rays in a CT scan, but the device according to the invention can also be used for other techniques such as Magnetic Resonance Imaging (MRI) or Positron emission tomography (PET). The fiducial marker is not always visible with optical means, especially if it is embedded in the device. The device can easily be provided with a landmark, i.e. an optical recognition mark visible from the outside, whose position and reference to the fiducial marker is precisely known. Such a landmark is especially useful if parts of the surgery are done manually. The landmark then serves as a guide for the surgeon.

According to the invention the means to fixate the device to the surgical instrument comprise a flat surface of the device and a mating surface on the surgical instrument, where one surface has protrusions that fit within indentations on the other surface. The surfaces then match and the protrusions and the indentations give a stable and well-defined coupling of the surfaces. The location of the indentations and the protrusions can be either on the device or on the surgical instrument, or on both as long as a protrusion on one surface matches an indentation on the other surface. The surfaces can then be clamped, bolted or screwed together to make a semi-permanent connection. The protrusions and the indentations make a well-defined fixation possible. The accuracy of the clamping, bolting or screwing is then not critical.

Preferably the protrusions are three cylindrical pins located along a line with their axis perpendicular to the surface they are located on. The cylindrical pins protruding from the surface fit in slots in the mating surface. In one direction the width of these slots corresponds to the diameter of the pins; in a perpendicular direction the length of the slots is larger than the pin diameter. This means that there are only two contact lines between the pin and the slot walls on the pin's circumference. Larger means in practice that the dimension of the length of the slot is around 10-20% larger than the diameter of the pins. Two pins or indentations are each located near opposite outer edges of the device and the third pin or indentation is located between the outer pins or indentations, for instance in the center of the device. The slots corresponding to the pins on the outer edges have the same dimension (width) as the pin in a direction perpendicular to the line and a larger dimension (length) in a direction along the line, the slot in between has the same dimension (width) as the pin in a direction along the line and a larger dimension (length) perpendicular to the line. For the pins located near the edge of the disk, i.e. the outer pins, the contact lines are in a tangential direction of the device; for the in between pin the contact lines are in a radial direction. Together the three locating pins, fitted in their respective slots, fixate the device for the two in plane translations between the device and the instrument and also for the rotation around the out of plane axis. Thus the pins and slots provide a kinematic coupling between the device and the surgical instrument. The device can have many shapes, like tri- or rectangular but preferably the device comprises an adapter disc. Such a shape fits easily to the skull. Preferably the disc has a contact surface between the mating surfaces of the device and the surgical instrument that is in the shape of a ring along the outer edge of the disc. This ring is slightly elevated from the rest of the surface. Such a contact ring prevents any out of plane, i.e. perpendicular to the contact surface, translation of the adapter disc. The pins, slots and the ring shaped contact surface between the disc and the instrument fully define the coordinates of the disc. The ring does not have to be fully closed, i.e. it can be made of parts of a ring.

As a material for the device a solid material translucent for the electromagnetic waves of the scan is used. There are many materials that can be used, like ceramics or plastics. Preferably the translucent material is Polyether ether ketone (PEEK). This material is strong and can easily be processed. This material is chosen based on its full compatibility, for instance in an MRI scan, its excellent machinability and availability as FDA-approved for medical appliance. Furthermore, from all technical polymers commonly available, it has superior mechanical properties, e.g. specific stiffness and a functional temperature window.

According to a further embodiment of the invention the device can be fixated to the skull with bone screws that fit in sleeves that protrude from the device. The sleeves protrude from the disc, so that they can be located within an opening of the skin on the skull. The length of the sleeves should be longer than the thickness of the skin, so that one end of the sleeves is directly in contact with the bone of the skull. The other end of the sleeves rests on the device. The skin is located around the sleeves. The screws are inside the sleeves and are screwed into the bone of the skull to fixate the device to the skull. Accordingly, the fixating forces of the device are directly transferred via the sleeves and the screws to the bone of the skull. This prevents skin becoming trapped between the device and the skull. Without the sleeves the resulting clamping force, applied to the skin over a prolonged period of time, could lead to skin damage, potentially even necrosis of the skin.

The sleeves can be separate components, but may also be integrated in the device, i.e. the adapter disc, for instance when the device is made by injection moulding, possibly with a different sizes for the disc: XS,S,M,L,XL.

In practice the skull of a patient can have many shapes. According to the invention it is advantageous for a good fixation to the skull if the device has a surface fixed to the skull that follows the contours of the skull at the location of that surface. Such a surface on the device can be made using an optical 3D scan of the skull and using these 3D scan data to modify a surface of the device that mates/fits with the surface of the skull. This is especially useful when the skull has a local deformation at the location the device needs to be fixated.

In the known device according to Weber et al. fiducial screws are used as markers. In practice the material of such screws is stainless steel or titanium. But these metals cause imaging artefacts such as flare in a scan. This makes it difficult to reference the scan data of the skull to the markers, especially when automated algorithms are used for referencing. According to the invention the fiducial marker comprises a cavity in the device filled with a liquid or pasty contrast agent. The cavity can be precisely shaped and located within the device. The contrast agent causes no artifacts and the accuracy with which the scan data can be linked to the fiducial marker greatly increases.

The contrast agent depends on the type of scan used. For MRI the contrast agent can be an aqueous solution of NaCl and $CUSO_4$. Accordingly the contrast required in the scan can be precisely adjusted to the waves used in the scan. For use in an MRI scan the preferred concentrations of the salts are determined empirically to be 700 mg $CuSO_4.5H_2O$ and 2000 mg NaCl in 1000 ml of demineralized water. For MRI also gadolinium contrast agents can be used. For a CT scan Iodine-based and barium-sulphate compounds can be used as contrast agents.

The cavity can have many shapes, like a star or rectangular shape. Preferably the cavity has the shape of a triangular groove. As the center of the triangle can be difficult to define, its coordinates can be easily deduced from the coordinates of the corners of the triangle. A choice should be made whether the inside or outside corners of the triangle groove or both are used (six points in total). The center point is then precisely defined as the vector average of the sum of all corner coordinate vectors. Another favorable shape is a circular groove that has a short radially pointing linear groove intersecting with the circular groove. Accordingly a center of the circle and a direction based on the direction of the line can be deduced.

The surgical instrument can operate on the patient away from the device, but it is advantageous when the device has a hole through which the surgical instrument can operate on the skull. The patient can rest on the device, i.e. the patient lies on the instrument and the device is pushed against the instrument. The instrument can operate from under the patient via the hole in the device. Any debris from the operation, like blood and bone splinters will then fall away from the operating area due to gravity. Traditional operations are not possible this way, since a surgeon needs to be able to see the operating area. Using the instrument from under the patient makes it very hard to see the operating area. The instrument however knows via the well-defined fixation of the device to the instrument, the coordinates of the skull exactly and can operate without optical help.

The invention also relates to the use of a device according to the invention in a surgical procedure.

DESCRIPTION FIGURES

The invention is further explained with the help of the following drawing in which FIG. 1 shows an instrument for deep brain stimulation that uses the device according to the invention.

Figure 1:
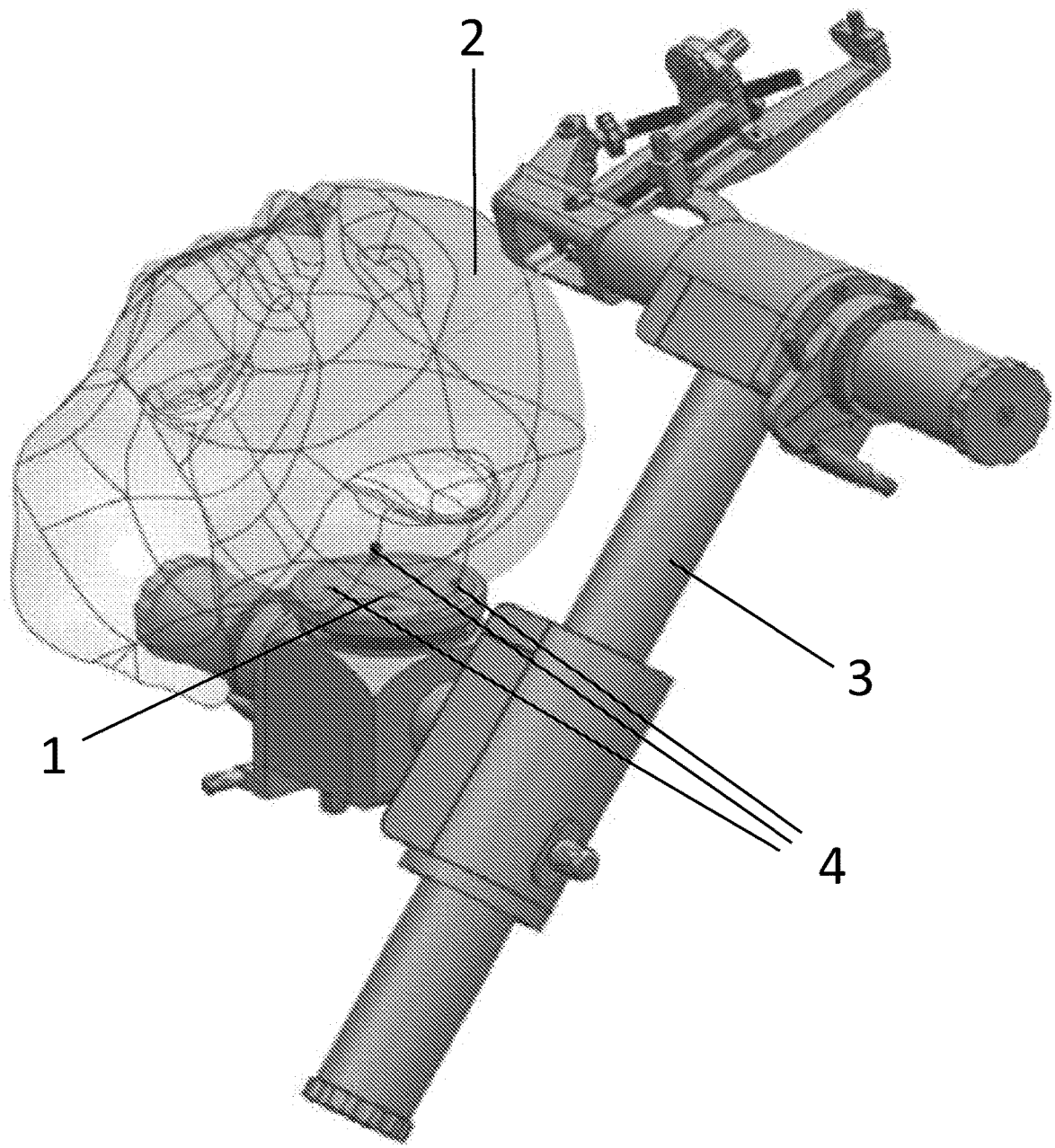

FIG. 1 shows a device 1 for fixation to the skull 2 of a patient. The device 1 can serve as a fiducial marker in scan guided surgical operations using a surgical instrument 3. The device 1 comprises a material translucent for the applied electromagnetic waves of the scan and a fiducial marker and where the device 1 comprises means to fixate the device 1 in a well-defined manner to the surgical instrument 3. The fiducial marker can be a traditional fiducial marker such as a fiducial screw or gold seed. Fiducial markers for different scanning methods are well known. In the device 1 a small gold seed is used as the fiducial marker (not shown). Such a marker has a small size (3×1 mm) and can be embedded in the device 1 by drilling a small hole and gluing the seed in place. The device 1 can be fixed to the surgical instrument 3 in a well-defined manner using for instance bolts or clamps. The device 1 can be fixated to the skull 2 by bone screws 4. The device 1 has the advantage that the data acquired with the scan can be directly referenced to the position of the surgical instrument 3, since the well-defined fixation of the device 1 to the surgical instrument 3 clearly defines the position of the fiducial marker(s), i.e. the position of the skull 2 with respect to the surgical instrument 3. The device 1 functions as an adapter (mechanical interface) between the skull 2 and the surgical instrument 3. Thus the device 1 functions as a shared reference for both the targeting scan and the fixation of the instrument 3 to the patient's head. The fiducial marker is not always visible with optical means, especially if it is embedded in the device. The device can easily be provided with a landmark, i.e. an optical recognition mark visible from the outside, which position and reference to the fiducial marker is precisely known.

The invention can be applied with many scanning techniques such as Magnetic Resonance Imaging (MRI), CT or Positron Emission Tomography (PET).

Figure 2:
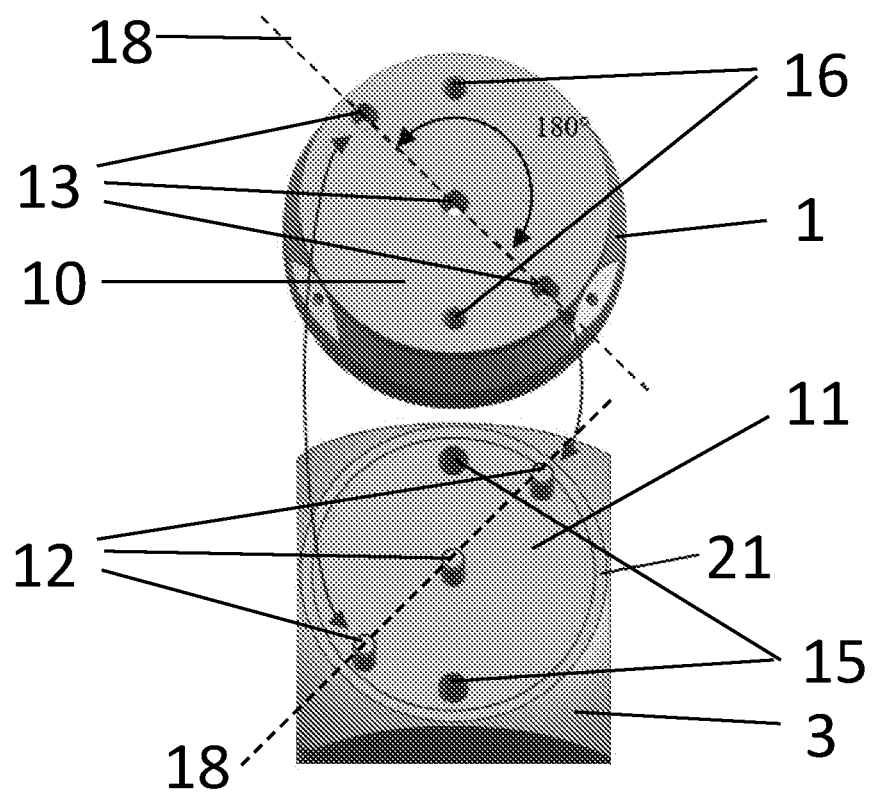
FIG. 2 shows the statically determined fixation of the device, i.e. an adapter disc to the surgical instrument.

FIG. 2 shows the means 12 and 13 to fixate the device 1 to a part of the surgical instrument 3. The means comprise a surface 10 of the device 1 and a mating surface 11 on the surgical instrument 3, where one surface 11 has protrusions 12 that fit within indentations 13 on the other surface 10. The protrusions 12 and indentations 13 can have many shapes as long as they fit into each-other. The surfaces 10, 11 then match and the protrusions 12 and the indentations 13 make a stable and well-defined coupling of the surfaces 10, 11 possible. The location of the indentations 13 and the protrusions 12 can be either on the device 1 or on a part of the surgical instrument 3, or on both as long as a protrusion 12 on one surface 10 or 11 matches an indentation 13 on the other surface 11 or 10. The surfaces 10, 11 can then be clamped or bolted together to make a semi-permanent connection.

Figure 3:
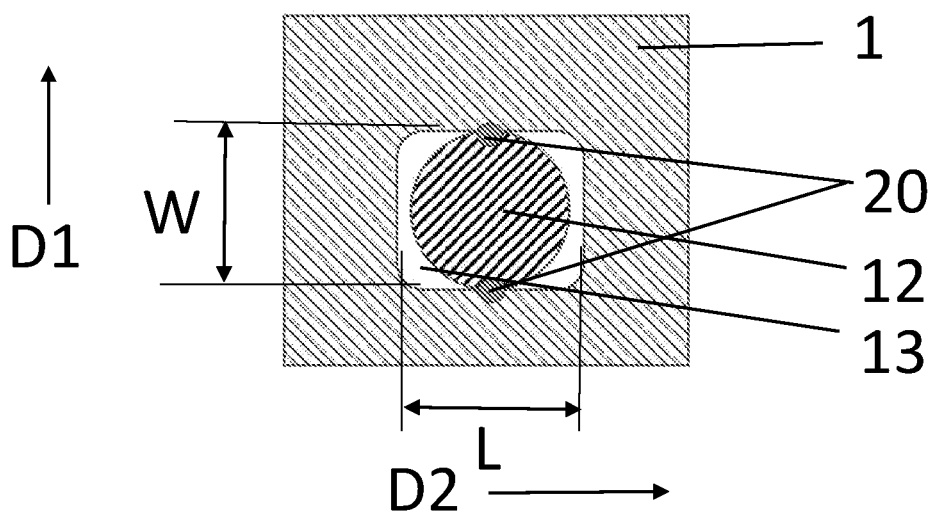
FIG. 3 shows how protrusions in the form of a cylinder fit in a rectangular slot.
Figure 4:
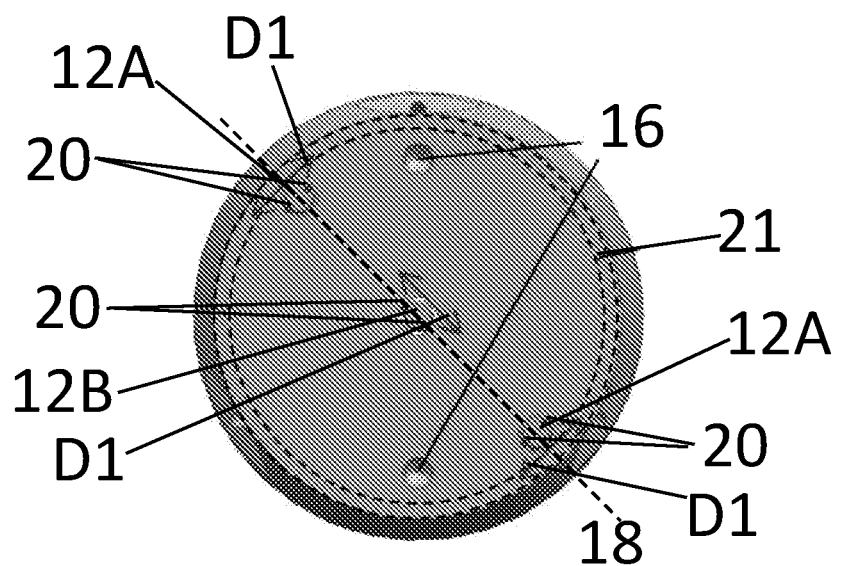
FIG. 4 shows a bottom view of the device with locating pins in rectangular slots; direction of fixation per pin indicated with arrows, contact lines with dots.

FIGS. 2, 3 and 4 shows that the protrusions 12 are three cylindrical pins 12 located along a line 18 with their axis perpendicular to a flat surface 11 they are located on. All three locating pins 12 protruding from the surface 11 to which the device 1 mounts, fit in rounded rectangular indentations (slots) 13 in the mating surface 10 of the device 1. FIG. 3 shows how the cylindrical pins 12 protruding from the surface 11 fit in slots 13 in the mating surface 10 (see FIG. 2). The width W of these slots 13 corresponds to the diameter of the pins 12; the length L of the slots 13 is slightly larger than the pin 12 diameter. There are only two contact lines 20 between each pin 12 and the slot 13 walls on the pin 12's circumference. Slightly larger means that the dimension of the length L of the slot 13 is around 10-20% larger than the diameter of the pins 12. This means that the pins 12 are only restricted in one direction D1 and are able to move slightly in the other direction D2. FIG. 4 shows that two pins 12A and the corresponding indentations 13 are each located near opposite outer edges of the device 1 and the third pin 12B and its corresponding indentation 13 is located between the outer pins 12A, for instance in the center of the device 1. The slots 13 corresponding to the pins 12A on the outer edges have the same dimension (width W) as the pin 12 in a direction D1 perpendicular to the line 18 and a slightly larger dimension (length L) in a direction along the line 18, the slot 13 in between corresponding to pin 12B has the same dimension (width W) as the pin 12 in a direction D1 along the line 18 and a slightly larger dimension (length L) perpendicular to the line 18. For the pins 12A located near the edge of the disk, i.e. the outer pins 12A, the contact lines 20 are in a tangential direction of the device 1; for the in between pin 12B the contact lines 20 are in a radial direction. Together the three locating pins 12A,B, fitted in their respective slots 13, fixate the two in-plane translations between the device 1 and the instrument 3 and also the relative rotation around the out-of-plane axis. Thus the pins 12 and slots 13 provide a kinematic coupling between the device 1 and the surgical instrument 3. This means every degree of freedom (DOF) in the coupling is fixed only once. The coupling of the means shown in FIGS. 2 and 4 is designed such that it can be closed in two ways separated by a relative rotation of 180 degrees. This value of 180 degrees follows naturally from the desire to setup the instrument 3 either along the right or left side of the patient's head. Furthermore, it simplifies the manufacturing process since the three slots 13 needed for the kinematic coupling now lie on a single line 18.

Figure 5:
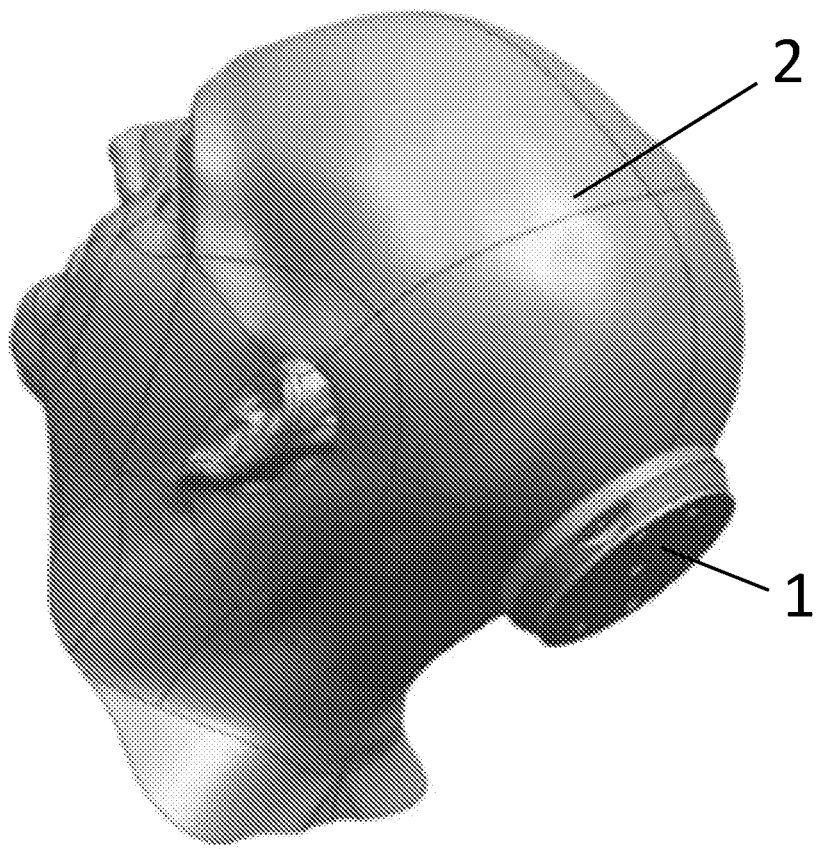
FIG. 5 shows how the device is fixated to the back of the head of a patient.

The device 1 can have many shapes, like tri- or rectangular but preferably the device 1 comprises an adapter disc. FIGS. 1 and 5 show how such a shape fits easily to the skull 2. FIGS. 2 and 4 show that the disc shaped device (disc) 1 has a contact surface between the mating surfaces 10,11 of the disc 1 and the surgical instrument 3 that is in the shape of a ring 21 along the outer edge of the disc 1. This ring is slightly elevated from the surface 11. Note well that the ring 21 need not be fully closed, i.e. it can be interrupted. When the disc 1 lands on the mating surface 11 of the instrument 3, it does so on the ring 21 with the same outer diameter as the disc's 1 contact surface and an inner diameter several millimeters smaller. This results in a ring-shaped contact surface fixating the out-of-plane, i.e. perpendicular to the contact surface, translation and the rotations around the two in-plane axes. After the disc 1 has landed, it is secured with two bolts approaching from underneath through holes 15 and fixated in threaded holes 16. When the bolts are tightened, the disc 1 is fixated by friction to the mating surface 11, with the ring-shaped surface 21 mentioned above as contact plane.

The pins 12, slots 13 and the ring shaped contact surface 21 between the disc 1 and the instrument 3 fully define the coordinates of the disc 1. The result is an extremely rigid and reliable connection which can be made and disassembled over and over without significant wear or loss of position.

The reproducibility of the coupling between the adapter disc 1 and the instrument 3, is determined by their manufacturing tolerances. For accurate manual machining work, a tolerance of ±0.01 mm can achieved for workpieces the size of the adapter disc 1, i.e. 100 mm.

The manufacturing tolerances on the position of the locating pins 12 on the instrument 3, and the corresponding slots 13 in the disc 1, result in play in the coupling between the disc 1 and the instrument 3. This play is primarily in the direction of the two in-plane translations between the disc 1 and the instrument 3, and the relative rotation around the out-of-plane axis.

For the two translations mentioned, the manufacturing tolerances of ±0.01 mm on the locations of both the pins 12 and slots 13, lead to a worst-case play of 0.04 mm in each respective direction. The relative rotation can have a worst-case play of 0.6 milliradians. As these play values can be present in the coupling between the instrument 3 and the adapter disc 1, they can be directly superimposed onto the accuracy of the instrument 3.

As a material for the device 1 a solid material translucent for the electromagnetic waves of the scan is used. Many materials can be used, like ceramics or plastics. For MRI the translucent material used is Polyether ether ketone (PEEK). This material is strong and can be easily processed. This material is chosen based on its full compatibility in an MRI scan, its excellent machinability and availability as FDA-approved for medical appliance. Furthermore, from all technical polymers commonly available, it has superior mechanical properties, e.g. specific stiffness and functional temperature window.

Figure 6:
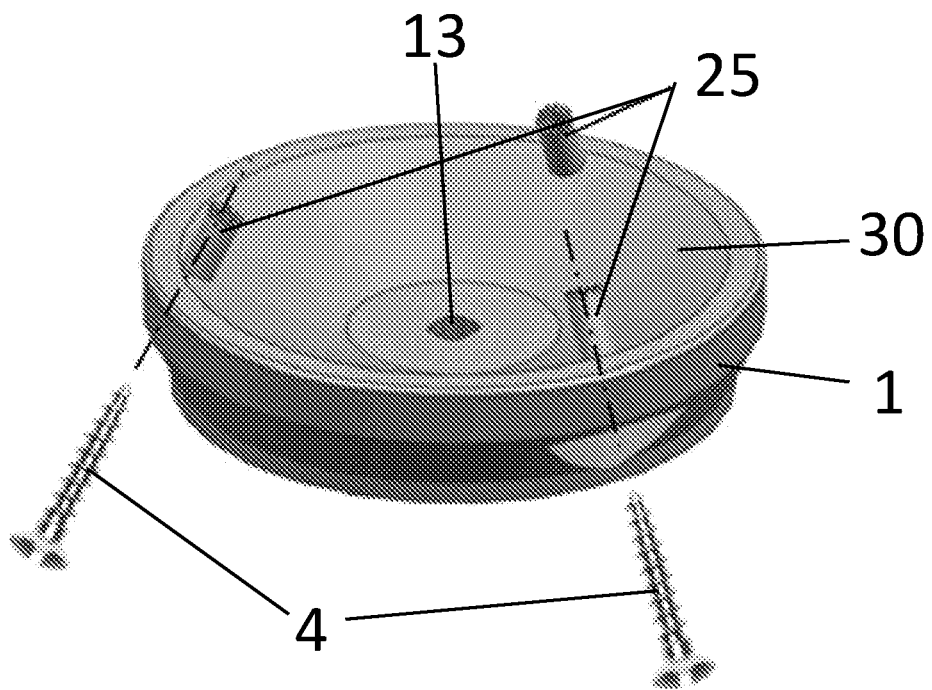
FIG. 6 shows how the device can be attached to the patient's head with three titanium sleeves and bone screws.
Figure 7:
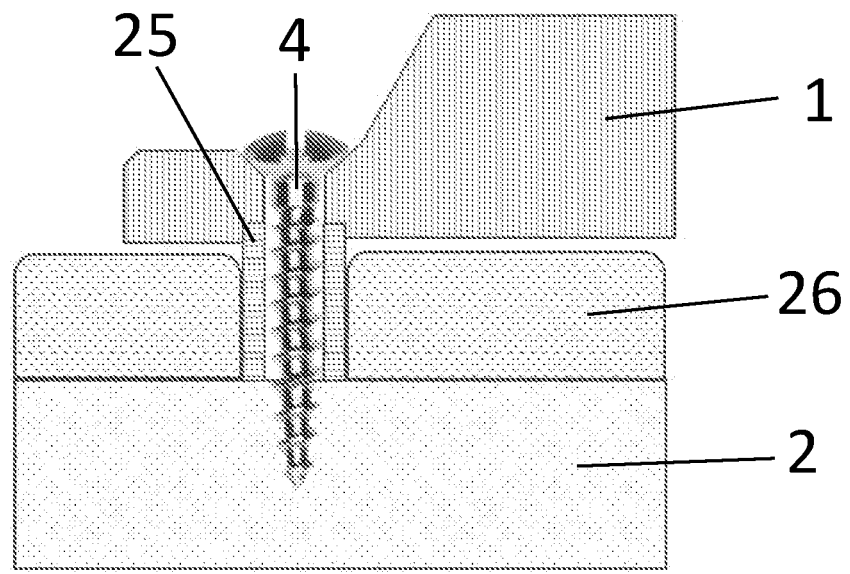
FIG. 7 shows a detail of FIG. 6.

FIGS. 6 and 7 show how the device, i.e. the adapter disc 1 is fixated to the skull 2 with bone screws 4 that fit in titanium sleeves 25 that protrude from the adapter disc 1. The adapter disc 1 is attached to the back of the patient's head (FIG. 5). The sleeves 25 protrude from the disc 1, so that they can be located within an opening of the skin 26 on the skull 2. These sleeves 25 and the bone screws 4 are the only components having invasive contact with the patient. The length of the sleeves 25 should be longer than the thickness of the skin 26, so that one end of the sleeves 25 is directly in contact with the bone of the skull 2. The other end of the sleeves 25 rests on the adapter disc 1. The skin 26 is located around the sleeves 25. The screws 4 are inside the sleeves 25 and are screwed into the bone of the skull 2 to fixate the adapter disc 1 to the skull 2. In this way, the fixating forces of the adapter disc 1 are directly transferred via the sleeves 25 and the screws 4 to the bone of the skull 2. This prevents skin 26 becoming trapped between the adapter disc 1 and the skull 2. Without the sleeves 25 the resulting clamping force, applied to the skin over a prolonged period of time, could lead to skin damage, potentially even necrosis of the skin. The sleeves 25 can be separate components, but may also be integrated in the adapter disc 1, for instance when the adapter disc 1 is produced directly by injection moulding. When one uses separate components, a titanium alloy is chosen as material for the sleeves 25, as this is compatible with scans like MRI and the material is inert in this specific environment.

In practice the skull 2 of a patient can have many shapes. In many cases a concave shape of the surface 30 of the device 1 that fits to the skull 2, as shown in FIG. 6, will fit to the skull 2 well. It is however advantageous for a good fixation to the skull 2 if the device 1 has a surface 30 that follows the contours of the skull 2 at the matching skull surface. Such a surface 30 on the device 1 can be made using an optical 3D scan of the skull 2 and using these 3D scan data to modify the device 1 so that it mates/fits with the surface of the skull 2. This is especially useful when the skull 2 has a local deformation at the location the device 1 needs to be fixated on.

Figure 8:
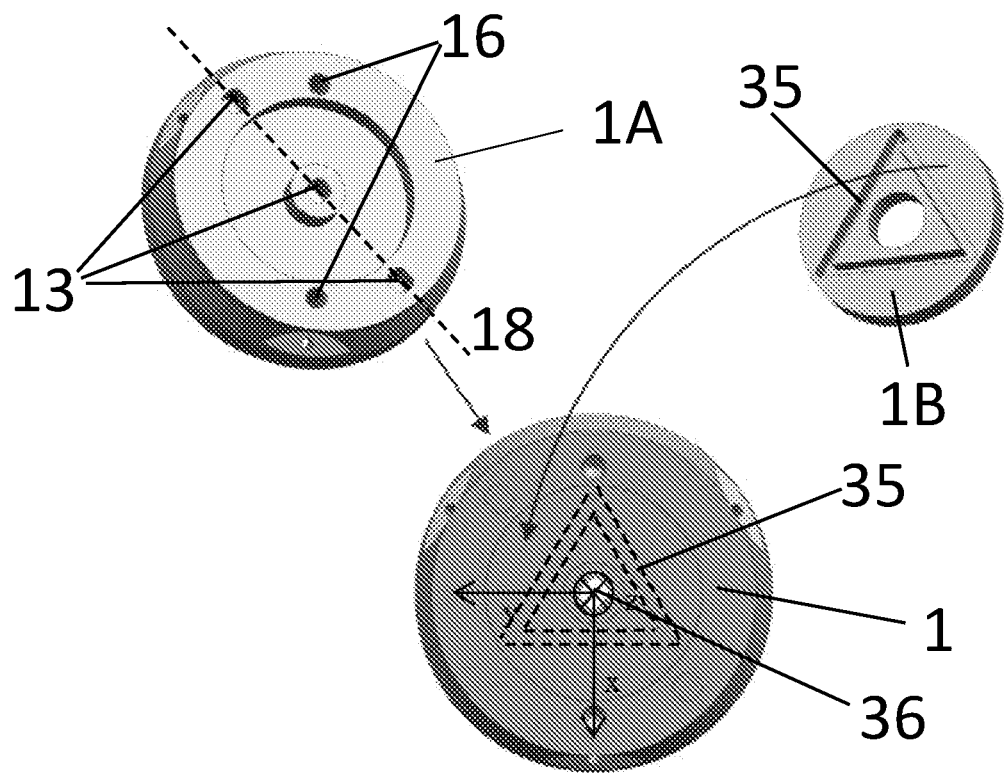
FIG. 8 shows how a fluid-containing cavity that serves as fiducial marker is realized in the PEEK device.

In the device known from Weber et al. fiducial screws 4 are used as markers. Also in the device 1 the screws 4 or sleeves 25 can be used as fiducial markers. In practice such screws 4 or sleeves 25 are made of stainless steel or titanium. But these metals cause imaging artefacts such as flare in a scan. Such flare reduces accuracy. This makes it difficult to reference the scan data of the skull 2 to the markers, especially when automated algorithms are used for referencing the scan data to the fiducial markers. FIG. 8 shows that the fiducial marker comprises a cavity 35 in the device 1 filled with a liquid or pasty contrast agent. The cavity 35 can be precisely shaped and located within the device 1. In FIG. 8 the device 1 is split up in a part 1A and a part 1B that comprises the cavity 35. The parts 1A and 1B fit together and form the device 1. The contrast agent depends on the type of scan used. For MRI the contrast agent can be an aqueous solution of NaCl and $CUSO_4$. In that way the contrast required in the scan can be precisely adjusted to the waves used in the scan. For use in an MRI scan the preferred concentrations of the salts are determined empirically to be 700 mg $CuSO_4.5H_2O$ and 2000 mg NaCl in 1000 ml of demineralized water. For MRI also gadolinium contrast agents can be used. For a CT scan Iodine-based and barium-sulfate compounds can be used as contrast agents.

To provide a usable reference for the targeting MRI scan, the PEEK adapter disc 1 features an internal cavity 35 filled with a solution of sodium chloride and copper sulfate in water. Although simple water would do, the relaxation times of the protons would in that case be longer than needed for the MRI scanner to produce a sharp image. This would result in a long scanning time. By adding the two salts mentioned, the relaxation time and thereby the scanning time are reduced. The ideal concentration of the salts in water is determined empirically to be 700 mg $CuSO_4.5H_2O$ and 2000 mg NaCl in 1000 ml of demineralized water.

The cavity 35 can have many shapes, like a star or rectangular shape. FIG. 8 shows how the cavity 35 containing the solution is shaped as a triangular groove 35. It is oriented such that one of its sides coincides with a reference y-axis and the other two sides point in the direction of the negative x-axis. The positive z-axis is oriented perpendicular to the plane of the triangle, in the direction of the patient's head. The center 36 of the triangle is identified as $(x,y,z)=(0,0,0)$. As the center 36 of the triangle can be hard to define in the MRI-images, its coordinates can be deduced from the coordinates of the corners. A choice should be made whether the inside or outside corners of the triangle are used, both of the upper and lower level of the triangle (six points in total). The center 36 point is then defined as the vector average of the sum of all corner coordinate vectors.

Another favorable shape for the cavity 35 is a circular groove that has a short radially pointing groove intersecting with the circular groove. In that way a center 36 of the circle and a direction based on the direction of the intersecting line can also be deduced easily.

Figure 9:
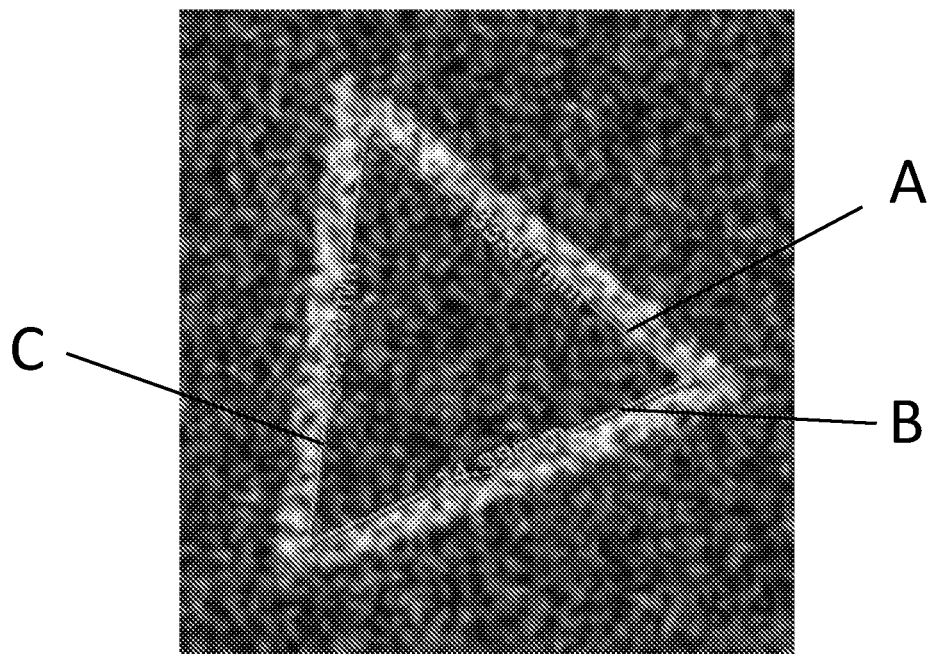
FIG. 9 shows the measurement of the fiducial marker triangle side lengths for a 150 mm Display Field of View (DFOV) scan.

The visibility of the marker has been verified using a Philips Medical Systems Intera 1.5T MRI scanner. FIG. 9 shows a resulting scan image from a slice with 0.5 millimeters thickness. The display field of view was 150 mm. The triangular reference marker can be made out clearly for the scan. The lengths A, B, C of the inner sides of the triangle have been measured with imaging software. For this, the corners have been selected as accurately as possible. This yielded values for A 33.67 mm, for B 34.39 mm and for C 34.31 mm. The real length, as would be measured with a caliper on the machined part, is 34.6 mm. As deduced from the measurement shown if FIG. 9 it becomes clear that the limited MRI resolution causes the inner sides to appear somewhat shorter (and the outer sides longer). As the largest deviation is less than three percent, the averaging used of the six corner coordinates to find the center 36 point coordinates, will nonetheless give an accurate value.

The following description shows an example how the disc 1 is used in a surgical procedure. As an example a deep brain stimulation surgical operation using an MRI scan will be described, but the device 1 can be used in other surgical procedures such as removing brain or jaw tumors or when implanting cochlear implants and when using scanning techniques other than MRI.

All steps in the procedure are preferably taken on one single day (see FIGS. 1, 5, 6, 7). That day starts with attaching a concave adapter disc 1 to the back of the patient's skull 2 by making small incisions in the skin 26 on the skull 2 of the patient. Titanium sleeves 25 with a slightly larger length than the thickness of the skin 26 are then inserted in the incisions, so that the sleeves 25 rest on the bone of the skull 2. Titanium bone screws 4 are inserted in holes in the adapter disc 1 and are screwed via the sleeves 25 into the bone of the skull 2. Thus the adapter disc 1 is firmly fixated to the patients head. An MRI scan is made of the patient's head, after which a stimulation target for the deep brain stimulation and an entry point for an electrode can be pointed out by the surgeon. Their coordinates are defined with respect to a clearly distinguishable landmark on the outside of the disc 1. The target and entry point coordinates will now be directly translated to instrument 3 settings via a mathematical algorithm which follows directly from the instrument 3's kinematics.

The location of fixation for the disc 1 on the back of the skull 2 is chosen so as to have minimal interference with the surgery and to provide enough bone thickness. Furthermore such a patient is in a supine position on an operating table. The adapter disc 1 will hereby land on its mating surface 11 on the instrument 3 base. The adapter disc 1 is then fixated to the base of the instrument 3 with two bolts though holes 15, 16. This position keeps the shear load on the screws 4 and sleeves 25 as a result of the head's weight to a minimum with the disc 1 placed on the back of the head. The local bone thickness is sufficient to support a rigid fixation with the screws 4 mentioned and resulting scars upon recovery lie within the patient's hair line.

A burr hole is made in the skull 2 manually, at the location indicated by the instrument 3. Fixation of the instrument 3 to the back of the patient's head ensures good visibility and access to the burr hole. With the burr hole made, the meninges can be opened by incision. The stimulation electrode can then be implanted with for instance a spindle that drives the electrode into the brain.

In this deep brain stimulation example the instrument 3 is also made of PEEK. Overall MRI compatibility of the instrument 3 then allows for electrode implantation under real-time MRI.

Combined with an optimized planning procedure, use of the adapter disc 1 gives a positioning accuracy an order of magnitude higher than what is achievable with the currently used deep brain stimulating instruments. The result is in an increase in surgery success rate.

The invention claimed is:

1. A device for fixation to the skull of a patient that can serve as a fiducial marker in scan guided surgical operations using a surgical instrument characterized in that the device comprises a material translucent for applied electromagnetic waves of the scan and a fiducial marker and where the device comprises means to fixate the device in a well-defined manner to the surgical instrument, wherein the means to fixate the device to the surgical instrument comprise a surface of the device and a mating surface on the surgical instrument, where one surface has protrusions that fit within indentations on the other surface, wherein the protrusions are three cylindrical pins located along a line with their axis perpendicular to a flat surface they are located on, where two pins or indentations are each located near opposite outer edges of the device and a third pin or indentation is located between outer pins and where the indentations corresponding to the pins are slots, where outer slots corresponding to the pins on the edges have the same dimension as the pin in a direction perpendicular to the line and a larger dimension in a direction along the line, the slot between the outer slots has the same dimension as the pin in a direction along the line and a larger dimension perpendicular to the line.

2. The device according to claim 1, characterized in that the device comprises an adapter disc where a contact surface between the mating surfaces of the device and the surgical instrument is in the shape of a ring along the outer edge of the disc.

3. The device according to claim 1, characterized in that the translucent material comprises Polyether ether ketone (PEEK) and that the scan is a magnetic resonance imaging (MRI) scan.

4. The device according to claim 1, characterized in that the device can be fixated to the skull with bone screws that fit in sleeves that protrude from the device.

5. The device according to claim 1, characterized in that a surface of the device fixed to the skull follows the contours of the skull at the location of that surface.

6. The device according to claim 1, characterized in that the fiducial marker comprises a cavity in the device filled with an liquid or pasty contrast agent.

7. The device according to claim 6, characterized in that a shape of the cavity is a triangular groove.

8. The device according to claim 1, characterized in that the device has a hole through which the surgical instrument can operate on the skull.

* * * * *